United States Patent
Wigglesworth et al.

(10) Patent No.: US 9,123,902 B2
(45) Date of Patent: Sep. 1, 2015

(54) SEMICONDUCTOR COMPOUND

(75) Inventors: Anthony J. Wigglesworth, Oakville (CA); Yiliang Wu, Oakville (CA); Ping Liu, Mississauga (CA)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 427 days.

(21) Appl. No.: 13/024,446

(22) Filed: Feb. 10, 2011

(65) Prior Publication Data
US 2012/0205630 A1  Aug. 16, 2012

(51) Int. Cl.
*H01L 51/00* (2006.01)
*C07D 495/06* (2006.01)
*H01L 51/05* (2006.01)

(52) U.S. Cl.
CPC .......... *H01L 51/0074* (2013.01); *C07D 495/06* (2013.01); *H01L 51/0076* (2013.01); *H01L 51/0541* (2013.01); *H01L 51/0545* (2013.01)

(58) Field of Classification Search
CPC ............................ C07D 495/02; C07D 495/06
USPC .......................................................... 549/24
See application file for complete search history.

(56) References Cited

U.S. PATENT DOCUMENTS

| | | | | |
|---|---|---|---|---|
| 5,281,489 | A * | 1/1994 | Mori et al. | 428/690 |
| 5,748,271 | A * | 5/1998 | Hikmet et al. | 349/69 |
| 6,835,471 | B2 * | 12/2004 | Tsuboyama et al. | 428/690 |
| 6,858,271 | B1 * | 2/2005 | Okada et al. | 428/1.4 |
| 6,897,913 | B2 * | 5/2005 | Tsuboyama et al. | 349/61 |
| 2009/0289248 | A1 | 11/2009 | Kobayashi et al. | |
| 2010/0013381 | A1 | 1/2010 | Stoessel et al. | |

OTHER PUBLICATIONS

Kobayashi et al., "Stable peri-Xanthenoxanthene Thin-Film Transistors with Efficient Carrier Injection," Chem. Mater. 2009, 21, 552-556.
Fabbri et al, "Preparation of Enantiomerically Pure 1,1'-Binaphthalene-2,2'-diol and 1,1'-Binaphthalene-2,2'-dithiol," J. Org. Chem. 1993, 58, 1748-1750.
Asari et al, "Charge-Transfer Complexes of PXX (PXX=6, 12-Dioxaanthanthrene). The Formal Charge and Molecular Geometry," Bull. Chem. Soc. Jpn., 74, 53-58 (2001).
Haryono et al., "Synthesis of a Novel Oligo(p-phenylene) Ladder by Sulfide and Sulfonio Groups," Macromolecules 1999, 32, 3146-3149.
Sirringhaus et al., "Dibenzothienobisbenzothiophene—a novel fused-ring oligomer with high field-effect mobility," J. Mater. Chem. 1999, 9, 2095-2101.
Wu et al., U.S. Appl. No. 12/977,464, filed Dec. 23, 2010.

* cited by examiner

*Primary Examiner* — Marie R. Yamnitzky
(74) *Attorney, Agent, or Firm* — Harness, Dickey & Pierce, P.L.C.

(57) ABSTRACT

A thiaxanthenothiaxanthene compound of Formula (I):

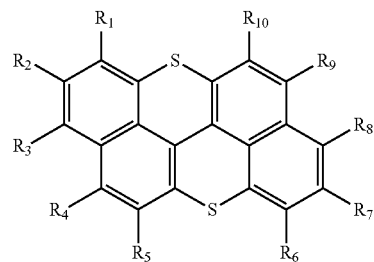

Formula (I)

wherein $R_1$ to $R_{10}$ are independently selected from the group consisting of hydrogen, an alkyl group, a substituted alkyl group, an alkoxy group, an alkylthio group, an alkenyl group, a substituted alkenyl group, an ethynyl group, a substituted ethynyl group, an aryl group, a substituted aryl group, a heteroaryl group, a substituted heteroaryl group, a trialkylsilyl group, a fluorohydrocarbon group, a cyano group and a halogen; and wherein the semiconductor of Formula (I) is predominantly crystalline or liquid crystalline. The compounds are designed to ensure air stability, good solubility, and high mobility.

7 Claims, 3 Drawing Sheets

SEMICONDUCTOR COMPOUND

BACKGROUND

The present disclosure relates to thin-film transistors (TFTs) and/or other electronic devices comprising a semiconducting layer. The semiconducting layer is formed from a semiconductor composition as described herein. When the composition is used in the semiconducting layer of a device, high mobility and excellent stability may be achieved.

TFTs are generally composed of, on a substrate, an electrically conductive gate electrode, source and drain electrodes, an electrically insulating gate dielectric layer which separate the gate electrode from the source and drain electrodes, and a semiconducting layer which is in contact with the gate dielectric layer and bridges the source and drain electrodes. Their performance can be determined by the field effect mobility and the current on/off ratio of the overall transistor. High mobility and high on/off ratio are desired.

Organic thin-film transistors (OTFTs) can be used in applications such as radio frequency identification (RFID) tags and backplane switching circuits for displays, such as signage, readers, and liquid crystal displays, where high switching speeds and/or high density are not essential. They also have attractive mechanical properties such as being physically compact, lightweight, and flexible.

Organic thin-film transistors can be fabricated using low-cost solution-based patterning and deposition techniques, such as spin coating, solution casting, dip coating, stencil/screen printing, flexography, gravure, offset printing, ink jet-printing, micro-contact printing, and the like. To enable the use of these solution-based processes in fabricating thin-film transistor circuits, solution processable materials are therefore required. However, organic or polymeric semiconductors formed by solution processing tend to suffer from limited solubility, air sensitivity, and especially low field-effect mobility. This poor performance may be attributable to the poor film-forming nature of small molecules.

It would be desirable to develop semiconducting compounds that exhibit high field effect mobility, air stability, and good solubility.

BRIEF DESCRIPTION

The present application discloses, in various embodiments, thiaxanthenothiaxanthene compounds of Formula (I):

Formula (I)

wherein $R_1$ to $R_{10}$ are independently selected from the group consisting of hydrogen, an alkyl group, a substituted alkyl group, an alkoxy group, an alkylthio group, an alkenyl group, a substituted alkenyl group, an ethynyl group, a substituted ethynyl group, an aryl group, a substituted aryl group, a heteroaryl group, a substituted heteroaryl group, a trialkylsilyl group, a fluorohydrocarbon group, a cyano group and a halogen; and wherein the semiconductor of Formula (I) is predominantly crystalline or liquid crystalline.

For field-effect transistor applications, thiaxanthenothiaxanthene compounds of Formula (I) are desired to be crystalline, or liquid crystalline.

In embodiments, at least one of $R_1$ to $R_{10}$ is not hydrogen. At least one of $R_1$ to $R_{10}$ may be a halogen. Alternatively, the substituent other than hydrogen may be selected from the group consisting of an alkyl group, a substituted alkyl group, an alkenyl group, a substituted alkenyl group, an ethynyl group, a substituted ethynyl group, an aryl group, a substituted aryl group, a heteroaryl group, a substituted heteroaryl group, and a halogen.

The thiaxanthenothiaxanthene compound may have the structure of Formula (II):

Formula (II)

wherein $R_2$ and $R_7$ are independently selected from the group consisting of hydrogen, an alkyl group, a substituted alkyl group, an alkoxy group, an alkylthio group, an alkenyl group, a substituted alkenyl group, an ethynyl group, a substituted ethynyl group, an aryl group, a substituted aryl group, a heteroaryl group, a substituted heteroaryl group, a trialkylsilyl group, a fluorohydrocarbon group, a cyano group, and a halogen.

In embodiments, at least one of $R_2$ and $R_7$ is not hydrogen. The substituent other than hydrogen may be selected from the group consisting of an alkyl group, a substituted alkyl group, an alkenyl group, a substituted alkenyl group, an ethynyl group, a substituted ethynyl group, an aryl group, a substituted aryl group, a heteroaryl group, a substituted heteroaryl group, and a halogen. $R_2$ and $R_7$ may be the same.

Also disclosed is a semiconductor composition comprising a polymer binder and a thiaxanthenothiaxanthene compound of Formula (I):

Formula (I)

wherein $R_1$ to $R_{10}$ are independently hydrogen, an alkyl group, a substituted alkyl group, an alkoxy group, an alkylthio group, an alkenyl group, a substituted alkenyl group, an ethynyl group, a substituted ethynyl group, an aryl group, a substituted aryl group, a heteroaryl group, a substituted heteroaryl group, a trialkylsilyl group, a fluorohydrocarbon group, a cyano group, and a halogen.

In some embodiments, $R_2$ and $R_7$ are the same and are selected from the group consisting of an alkyl group, a substituted alkyl group, an alkenyl group, a substituted alkenyl group, an ethynyl group, a substituted ethynyl group, an aryl group, a substituted aryl group, a heteroaryl group, a substituted heteroaryl group, and a halogen. In further embodiments, $R_2$ and $R_7$ are the same and are selected from the group described above, while $R_1$, $R_3$, $R_4$, $R_5$, $R_6$, $R_7$, $R_8$ and $R_{10}$ are hydrogen.

The polymer binder may be polymethylmethacrylate, polystyrene, poly(α-methyl styrene), poly(4-methyl styrene), poly(α-methyl styrene-co-vinyl toluene), poly(styrene-block-butadiene-block-styrene), poly(styrene-block-isoprene-block-styrene), poly(vinyl toluene), poly(vinyl naphthalene), poly(vinyl pyridine), terpene resin, poly(styrene-co-2,4-dimethylstyrene), poly(chlorostyrene), poly(styrene-co-α-methyl styrene), poly(styrene-co-butadiene), polycarbazole, and polytriarylamine, or poly(N-vinylcarbazole), polythiophene, or mixtures thereof.

The weight ratio of the thiaxanthenothiaxanthene compound to the polymer binder may be from 5:1 to 2:3.

Further disclosed is an electronic device comprising a semiconducting layer, wherein the semiconducting layer comprises a thiaxanthenothiaxanthene compound of Formula (I):

Formula (I)

wherein $R_1$ to $R_{10}$ are independently selected from the group consisting of hydrogen, an alkyl group, a substituted alkyl group, an alkoxy group, an alkylthio group, an alkenyl group, a substituted alkenyl group, an ethynyl group, a substituted ethynyl group, an aryl group, a substituted aryl group, a heteroaryl group, a substituted heteroaryl group, a trialkylsilyl group, a fluorohydrocarbon group, a cyano group and a halogen; and wherein the semiconductor of formula (I) is predominantly crystalline or liquid crystalline.

In embodiments, at least one of $R_1$ to $R_{10}$ is not hydrogen. At least one of $R_1$ to $R_{10}$ may be a halogen.

The semiconducting layer further comprises a polymer binder. The polymer binder may be polymethylmethacrylate, polystyrene, poly(α-methyl styrene), poly(4-methyl styrene), poly(α-methyl styrene-co-vinyl toluene), poly(styrene-block-butadiene-block-styrene), poly(styrene-block-isoprene-block-styrene), poly(vinyl toluene), poly(vinyl naphthalene), poly(vinyl pyridine), terpene resin, poly(styrene-co-2,4-dimethylstyrene), poly(chlorostyrene), poly(styrene-co-α-methyl styrene), poly(styrene-co-butadiene), polycarbazole, and polytriarylamine, or poly(N-vinylcarbazole), polythiophene, or mixtures thereof.

The weight ratio of thiaxanthenothiaxanthene compound to the polymer binder may be from 5:1 to 2:3.

The electronic device may be a field-effect transistor.

The electronic device may further comprise a dielectric layer. The dielectric layer comprises a modified surface. The semiconductor layer is in direct contact with the modified surface. The modified surface may have been modified by an organosilane.

These and other non-limiting characteristics of the disclosure are more particularly disclosed below.

BRIEF DESCRIPTION OF THE DRAWINGS

The following is a brief description of the drawings, which are presented for the purposes of illustrating the exemplary embodiments disclosed herein and not for the purposes of limiting the same.

DETAILED DESCRIPTION

A more complete understanding of the components, processes and apparatuses disclosed herein can be obtained by reference to the accompanying drawings. These figures are merely schematic representations based on convenience and the ease of demonstrating the present disclosure, and are, therefore, not intended to indicate relative size and dimensions of the devices or components thereof and/or to define or limit the scope of the exemplary embodiments.

Although specific terms are used in the following description for the sake of clarity, these terms are intended to refer only to the particular structure of the embodiments selected for illustration in the drawings, and are not intended to define or limit the scope of the disclosure. In the drawings and the following description below, it is to be understood that like numeric designations refer to components of like function.

The modifier "about" used in connection with a quantity is inclusive of the stated value and has the meaning dictated by the context (for example, it includes at least the degree of error associated with the measurement of the particular quantity). When used in the context of a range, the modifier "about" should also be considered as disclosing the range defined by the absolute values of the two endpoints. For example, the range of "from about 2 to about 10" also discloses the range "from 2 to 10".

The term "comprising" is used herein as requiring the presence of the named component and allowing the presence of other components. The term "comprising" should be construed to include the term "consisting of", which allows the presence of only the named component, along with any impurities that might result from the manufacture of the named component.

The term "predominantly" refers to a value of greater than 50%.

The present disclosure relates to thiaxanthenothiaxanthene compounds as disclosed herein. The compounds exhibit good solubility. Compositions comprising a polymer binder and the thiaxanthenothiaxanthene compound are also disclosed. A semiconducting layer formed from the composition is very stable in air and has high mobility. These semiconductor compositions are useful for forming layers in electronic devices, such as thin-film transistors (TFTs).

Figure 1:
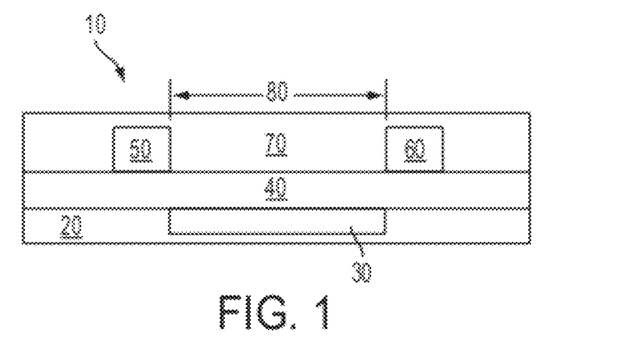
FIG. 1 is a diagram of a first embodiment of a TFT according to the present disclosure.

FIG. 1 illustrates a bottom-gate bottom-contact TFT configuration according to the present disclosure. The TFT 10 comprises a substrate 20 in contact with the gate electrode 30 and a gate dielectric layer 40. The gate electrode 30 is depicted here in a depression within the substrate 20, but the gate electrode could also be located atop the substrate. It is important that the gate dielectric layer 40 separates the gate electrode 30 from the source electrode 50, drain electrode 60, and the semiconducting layer 70. The semiconducting layer 70 runs over and between the source and drain electrodes 50 and 60. The semiconductor has a channel length 80 between the source and drain electrodes 50 and 60.

Figure 2:
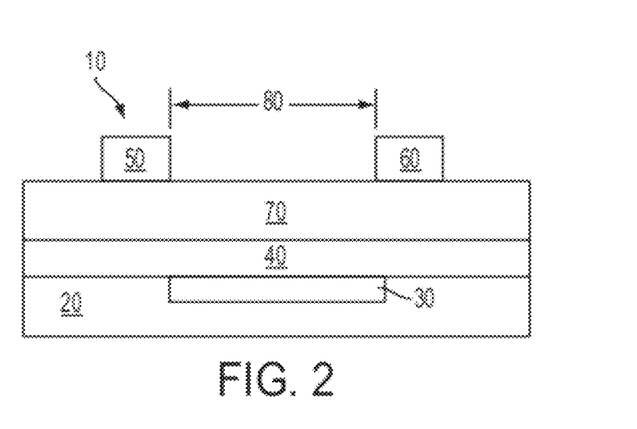
FIG. 2 is a diagram of a second embodiment of a TFT according to the present disclosure.

FIG. 2 illustrates another bottom-gate top-contact TFT configuration according to the present disclosure. The TFT 10 comprises a substrate 20 in contact with the gate electrode 30 and a gate dielectric layer 40. The semiconducting layer 70 is placed on top of the gate dielectric layer 40 and separates it from the source and drain electrodes 50 and 60.

Figure 3:
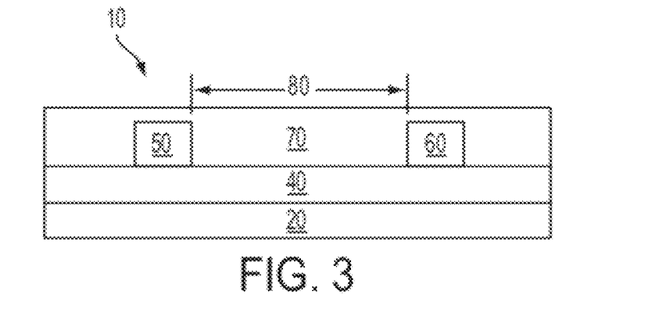
FIG. 3 is a diagram of a third embodiment of a TFT according to the present disclosure.

FIG. 3 illustrates a bottom-gate bottom-contact TFT configuration according to the present disclosure. The TFT 10 comprises a substrate 20 which also acts as the gate electrode and is in contact with a gate dielectric layer 40. The source electrode 50, drain electrode 60, and semiconducting layer 70 are located atop the gate dielectric layer 40.

Figure 4:
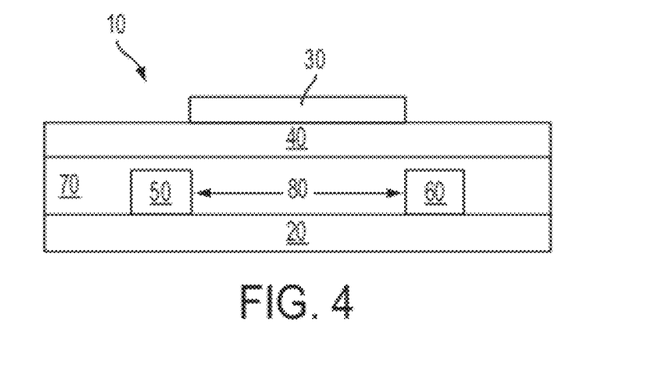
FIG. 4 is a diagram of a fourth embodiment of a TFT according to the present disclosure.

FIG. 4 illustrates a top-gate top-contact TFT configuration according to the present disclosure. The TFT 10 comprises a substrate 20 in contact with the source electrode 50, drain electrode 60, and the semiconducting layer 70. The semiconducting layer 70 runs over and between the source and drain electrodes 50 and 60. The gate dielectric layer 40 is on top of the semiconducting layer 70. The gate electrode 30 is on top of the gate dielectric layer 40 and does not contact the semiconducting layer 70.

The thiaxanthenothiaxanthene compound has the structure of Formula (I):

Formula (I)

wherein $R_1$ and $R_{10}$ are independently hydrogen, an alkyl group, a substituted alkyl group, an alkoxy group, an alkylthio group, an alkenyl group, a substituted alkenyl group, an ethynyl group, a substituted ethynyl group, an aryl group, a substituted aryl group, a heteroaryl group, a substituted heteroaryl group, a trialkylsilyl group, a fluorohydrocarbon group, a cyano group, and a halogen. The thiaxanthenothiaxanthene compound may also be referred to as a thioxanthenothioxanthene compound.

When $R_1$ to $R_{10}$ are hydrogen, the thiaxanthenothiaxanthene compound, which has no substituents, may be abbreviated herein as "TXTX". In embodiments, at least one of $R_1$ to $R_{10}$ is not hydrogen. The molecule of Formula (I) is also known as 2,8-disubstituted thiaxanthenothiaxanthene when neither $R_2$ nor $R_7$ is hydrogen. For example, the semiconductor of Formula (I) could be referred to as 2,8-disubstituted-TXTX.

The term "alkyl" refers to a radical composed entirely of carbon atoms and hydrogen atoms which is fully saturated. The alkyl radical may be linear, branched, or cyclic.

The term "alkenyl" refers to a radical composed entirely of carbon atoms and hydrogen atoms which contains at least one carbon-carbon double bond that is not part of an aryl or heteroaryl structure. The alkenyl radical may be linear, branched, or cyclic.

The term "aryl" refers to an aromatic radical composed entirely of carbon atoms and hydrogen atoms. When aryl is described in connection with a numerical range of carbon atoms, it should not be construed as including substituted aromatic radicals. For example, the phrase "aryl containing from 6 to 10 carbon atoms" should be construed as referring to a phenyl group (6 carbon atoms) or a naphthyl group (10 carbon atoms) only, and should not be construed as including a methylphenyl group (7 carbon atoms).

The term "heteroaryl" refers to an aromatic radical composed of carbon atoms, hydrogen atoms, and one or more heteroatoms. The carbon atoms and the heteroatoms are present in a cyclic ring or backbone of the radical. The heteroatoms are selected from O, S, and N. Exemplary heteroaryl radicals include thienyl (an aromatic radical of the formula —$C_4H_3S$ formed by removing a hydrogen atom from thiophene) and pyridinyl. When heteroaryl is described in connection with a numerical range of carbon atoms, it should not be construed as including substituted heteroaromatic radicals.

The term "ethynyl" refers to a radical of the formula —C≡C—H.

The term "alkoxy" refers to an alkyl radical which is attached to an oxygen atom, i.e. —O—$C_nH_{2n+1}$.

The term "alkylthio" refers to an alkyl radical which is attached to a sulfur atom, i.e. —S—$C_nH_{2n+1}$.

The term "trialkylsilyl" refers to a radical composed of a tetravalent silicon atom having three alkyl radicals attached to the silicon atom, i.e. —$Si(R)_3$. The three alkyl radicals may be the same or different. The three alkyl radicals may be substituted.

The term "fluorohydrocarbon" refers to a radical composed entirely of fluorine, hydrogen, and carbon atoms. At least one fluorine atom must be present. The radical can be linear or branched, and is usually saturated.

The term "substituted" refers to at least one hydrogen atom on the named radical being substituted with another functional group, such as halogen, —CN, —$NO_2$, —COOH, and —$SO_3H$. An exemplary substituted alkyl group is a perhaloalkyl group, wherein one or more hydrogen atoms in an alkyl group are replaced with halogen atoms, such as fluorine, chlorine, iodine, and bromine. Besides the aforementioned functional groups, an alkyl, alkenyl, or ethynyl group may also be substituted with an aryl or heteroaryl group. An exemplary substituted alkenyl group is phenylethenyl (—CH═CH—$C_6H_5$). An exemplary substituted ethynyl group is phenylethynyl (—C≡C—$C_6H_5$). An aryl or heteroaryl group may also be substituted with alkyl or alkoxy. Exemplary substituted aryl groups include methylphenyl and methoxyphenyl. Exemplary substituted heteroaryl groups include 3-hexyl-thiophene-2,5-diyl.

Generally, the alkyl and alkoxy groups each independently contain from 1 to 30 carbon atoms. Similarly, the aryl groups independently contain from 6 to 30 carbon atoms.

As noted above, $R_1$ to $R_{10}$ may be the same or different. In specific embodiments, at least one of $R_1$ to $R_{10}$ is not hydrogen. In more specific embodiments, the substituent that is not hydrogen is selected from the group consisting of an alkyl group, a substituted alkyl group, an alkenyl group, a substituted alkenyl group, an ethynyl group, a substituted ethynyl group, an aryl group, a substituted aryl group, a heteroaryl group, a substituted heteroaryl group, and a halogen. In more specific embodiments, the substituent that is not hydrogen is a halogen. In other particular embodiments, two of the $R_1$ to $R_{10}$ substituents are not hydrogen.

In particular embodiments, $R_1$, $R_3$ to $R_6$, and $R_8$ to $R_{10}$ are hydrogen. The compound then has the structure of Formula (II):

Formula (II)

wherein $R_2$ and $R_7$ are independently hydrogen, an alkyl group, a substituted alkyl group, an alkoxy group, an alkylthio group, an alkenyl group, a substituted alkenyl group, an ethynyl group, a substituted ethynyl group, an aryl group, a substituted aryl group, a heteroaryl group, a substituted heteroaryl group, a trialkylsilyl group, a fluorohydrocarbon group, a cyano group, and a halogen.

The compound of Formula (II) is also known as a 2,8-disubstituted thiaxanthenothiaxanthene when neither $R_2$ nor $R_7$ is hydrogen. The semiconductor compound of Formula (II) could also be referred to as 2,8-disubstituted-TXTX.

The compound of Formula (I) is preferably predominantly crystalline or liquid crystalline. In particular embodiments, the compound or semiconducting layers formed from the compound may exhibit a crystallinity greater than about 50%. In embodiments, the compound or semiconducting layer may have a crystallinity of greater than about 80%, or greater than about 90%. The crystallinity of the semiconductor layer can be determined using any suitable method, for example an X-ray diffraction method.

The term liquid crystalline refers to compounds which have at least two melting points. The phase transition temperatures can be determined using any suitable method, for example by a differential scanning calorimetry method. In contrast, crystalline compounds have only one melting point.

In embodiments, the thiaxanthenothiaxanthene compound has a band gap of from about 1.8 to about 3.2 eV. This band gap typically means that the thiaxanthenothiaxanthene compound has better stability in air, when compared to a pentacene-based semiconductor. The thiaxanthenothiaxanthene compound has a crystalline or liquid crystalline structure.

Methods of producing the thiaxanthenothiaxanthene compound of Formula (II) generally begin with the synthesis of the TXTX compound. It is believed that hydrogen atoms at the 2- and 8-positions of the TXTX compound can then be replaced with the desired substituents to produce 2-monosubstituted-TXTX, 8-monosubstituted-TXTX, and/or 2,8-disubstituted-TXTX.

The TXTX core compound may be formed from at least two synthetic routes. In the first route, Cu(II)-mediated double cyclization is used to synthesize the TXTX core compound directly from 1,1'-binaphthalene-2,2'-dithiol 1. This reaction is shown below:

In the second route, 1,1'-binaphthalene2,2'-dithiol 1 is converted to 2,2'-bis(methylsulfinyl)-1,1'-binaphthalene 2 via methylation and subsequent oxidation with hydrogen peroxide as shown below:

Next, the 2,2'-bis(methylsulfinyl)1-1'-binaphthalene 2 is converted to the TXTX core using a triflic acid-mediated electrophilic ring closure followed by demethylation as illustrated below:

It is believed that the TXTX core compound can be functionalized, i.e. substituted at the 2- and/or 8-positions, by a variety of methods. Two such routes are discussed below.

Figure 5:
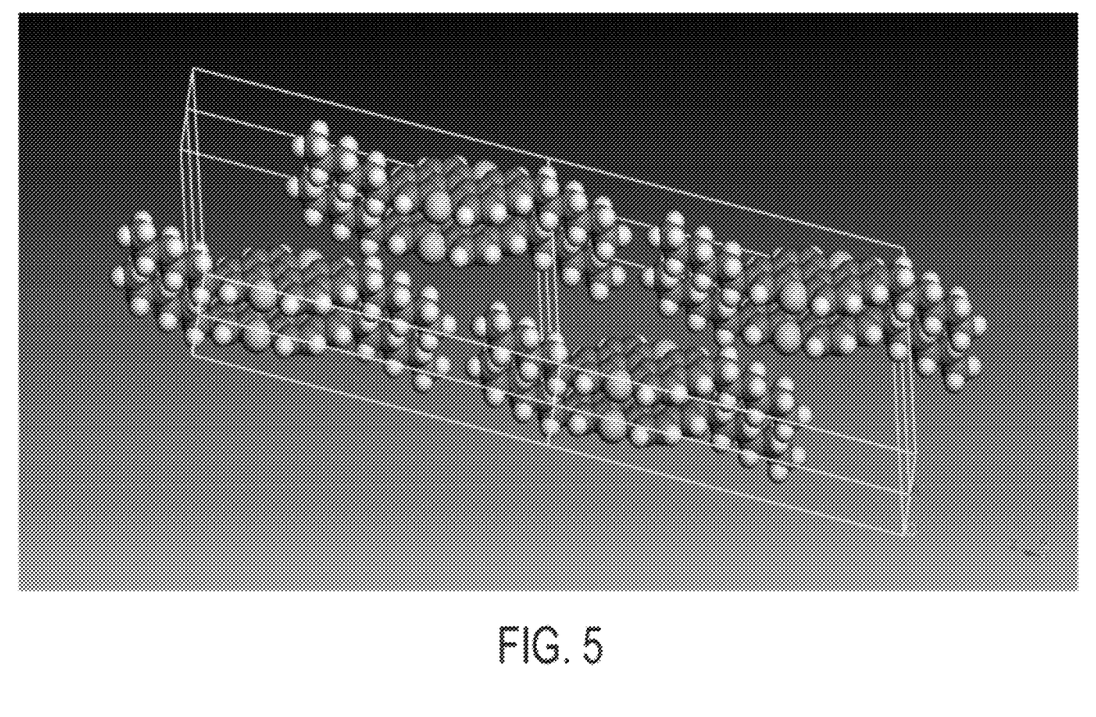
FIG. 5 shows a color model of the equilibrium geometry and simulated crystal structure of 2,8-dihexyl thiaxanthenothiaxanthene.

The first route is designed to produce 2,8-dialkyl substituted TXTX from the TXTX core using a two step procedure. In the first step, the TXTX core undergoes Freidel-Crafts acylation to produce 2,8-diacyl substituted TXTX 3. This reaction is illustrated below:

In the second step, the 2,8-diacyl substituted TXTX 3 is reduced by Wolfe-Kishner reduction to produce 2,8-dialkyl substituted TXTX 4. This reaction is shown below:

The second route is designed to produce 2,8-diaryl substituted TXTX. In the illustrative reaction, the aryl group is phenyl. First, the TXTX core is brominated to form a 2,8-dibromo-TXTX 5 as depicted below:

Next, the 2,8-dibromo-TXTX 5 undergoes a Pd-catalyzed cross-coupling reaction, such as a Suzuki-Miyaura coupling reaction, to produce the 2,8-diaryl substituted TXTX 6 as shown below:

FIG. 5 illustrates a color molecular model of 2,8-dihexyl TXTX, i.e. a compound of Formula (I) wherein $R_1$ and $R_2$ are hexyl. The model shows the equilibrium geometry and crystal structure of the compound. The model formed in Materials Studio 5.0 using the DMol3 package and the crystal structure prediction was performed using the Polymorph module. Without being bound by theory, it is believed that the sulfur heteroatoms aid stability, the extended heteroacene core enhances orbital overlap, and the substitutions at the 2- and 8-positions aid solubility and enhance solid-state packing. The compounds are designed to ensure air stability, good solubility, and high mobility. Electronic devices including a semiconducting layer comprising the compounds may be produced at a low cost under ambient conditions.

The small molecule semiconductor by itself may have poor film-forming properties, which is attributed to its crystalline or liquid crystalline nature. Thus, the semiconductor composition may also comprise a polymer binder, which allows a uniform film to be achieved, significantly improving device performance. The polymer binder can be considered as forming a matrix within which the thiaxanthenothiaxanthene compound is dispersed.

Any suitable polymer can be used as the polymer binder for the semiconductor composition. In some embodiments, the polymer is an amorphous polymer. The amorphous polymer may have a glass transition temperature less than the melting point temperature of the small molecule semiconductor of Formula (I). In other embodiments, the amorphous polymer has a glass transition temperature greater than the melting point temperature of the small molecule semiconductor. In embodiments, the polymer has a dielectric constant less than 4.5, preferably less than 3.5, including less than 3.0, as measured at 60 Hz at room temperature. In embodiments, the polymer is selected from polymers containing only C, H, F, Cl, and/or N atoms. In some embodiments, the polymer is a low polarity polymer such as a hydrocarbon polymer or a fluorocarbon polymer without any polar groups. For example, polystyrene is an amorphous polymer and has a dielectric constant about 2.6. A list of other low polarity polymers includes, but is not limited to, the following: fluoropolyarylether, poly(p-xylylene), poly(vinyl toluene), poly(α-methyl styrene), poly(a-vinylnaphthalene), polyethylene, polypropylene, polyisoprene, poly(tetrafluoroethylene), poly(chlorotrifluoroethylene), poly(2-methyl-1,3-butadiene), poly(cyclohexyl methacrylate), poly(chlorostyrene), poly(4-methyl styrene), poly(vinyl, cyclohexane), polyphenylene, poly-p-phenylvinylidenes, poly(arylene ether), polyisobutylene, poly(2,6-dimethyl-1,4-phenylene ether), poly[1,1-(2-methyl propane) bis-(4-phenyl)carbonate], poly(α-α-α'-α'tetrafluoro-p-xylylene), fluorinated polyimide, poly(ethylene/tetrafluoroethylene), poly(ethylene/chlorotrifluoroethylene), fluorinated ethylene/propylene copolymer, poly(styrene-co-α-methyl styrene), poly(styrene/butadiene), poly(styrene/2,4-dimethylstyrene), CYTOP, poly(propylene-co-1-butene), poly(styrene-co-vinyl toluene), poly(styrene-block-butadiene-block-styrene), poly(styrene-block-isoprene-block-styrene), a terpene resin, poly(N-vinylcarbazole), polycarbazole, a polytriarylamine, and the like.

The weight ratio of the thiaxanthenothiaxanthene compound to the polymer binder may be from 5:1 to 2:3.

The semiconductor composition may further comprise a solvent in which the thiaxanthenothiaxanthene compound and the polymer binder are soluble. Exemplary solvents used in the solution may include chlorinated solvents such as chlorobenzene, chlorotoluene, dichlorobenzene, dichloroethane, and the like; alcohols and diols such as propanol, butanol, hexanol, hexanediol, etc.; hydrocarbons or aromatic hydrocarbons such as hexane, heptane, toluene, xylene, mesitylene, ethyl benzene, etc.; ketones such as acetone, methyl ethyl ketone, etc.; acetates, such as ethyl acetate; pyridine, tetrahydrofuran, dioxane, and the like.

In embodiments, the semiconductor composition comprising the thiaxanthenothiaxanthene compound and the polymer binder may have a viscosity of from about 1.5 centipoise (cps) to about 100 cps, including from about 2 to about 20 cps.

The semiconducting layer may be formed in an electronic device using conventional processes known in the art. In embodiments, the semiconducting layer is formed using solution depositing techniques. Exemplary solution depositing techniques include spin coating, blade coating, rod coating, dip coating, screen printing, ink jet printing, stamping, stencil printing, screen printing, gravure printing, flexography printing, and the like.

The semiconducting layer formed using the semiconductor composition can be from about 5 nanometers to about 1000 nanometers deep, including from about 20 to about 100 nanometers in depth. In certain configurations, such as the configurations shown in FIGS. 1 and 4, the semiconducting layer completely covers the source and drain electrodes.

The performance of a TFT can be measured by mobility. The mobility is measured in units of $cm^2/V\cdot sec$; higher mobility is desired. The resulting TFT using the semiconductor composition of the present disclosure may have a field effect mobility of at least about 0.01 $cm^2/V\cdot sec$. The TFT of the present disclosure may have a current on/off ratio of at least about $10^3$.

A thin film transistor generally includes a substrate, an optional gate electrode, source electrode, drain electrode, and a dielectric layer in addition to the semiconducting layer.

The substrate may be composed of materials including but not limited to silicon, glass plate, plastic film or sheet. For structurally flexible devices, plastic substrate, such as for example polyester, polycarbonate, polyimide sheets and the like may be preferred. The thickness of the substrate may be from about 10 micrometers to over 10 millimeters with an exemplary thickness being from about 50 to about 100 micrometers, especially for a flexible plastic substrate and from about 0.5 to about 10 millimeters for a rigid substrate such as glass or silicon.

The dielectric layer generally can be an inorganic material film, an organic polymer film, or an organic-inorganic composite film. Examples of inorganic materials suitable as the dielectric layer include silicon oxide, silicon nitride, aluminum oxide, barium titanate, barium zirconium titanate and the like. Examples of suitable organic polymers include polyesters, polycarbonates, poly(vinyl phenol), polyimides, polystyrene, polymethacrylates, polyacrylates, epoxy resin and the like. The thickness of the dielectric layer depends on the dielectric constant of the material used and can be, for example, from about 10 nanometers to about 500 nanometers. The dielectric layer may have a conductivity that is, for example, less than about $10^{-12}$ Siemens per centimeter (S/cm). The dielectric layer is formed using conventional processes known in the art, including those processes described in forming the gate electrode.

In the present disclosure, the dielectric layer may be surface modified with a surface modifier. Exemplary surface modifiers include organosilanes such as hexamethyldisilazane (HMDS), octyltrichlorosilane (OTS-8), octadecyltrichlorosilane (ODTS-18), and phenyltrichlorosilane (PTS). The semiconducting layer can be directly contacted with this modified dielectric layer surface. The contact may be complete or partial. This surface modification can also be considered as forming an interfacial layer between the dielectric layer and the semiconducting layer.

The gate electrode is composed of an electrically conductive material. It can be a thin metal film, a conducting polymer film, a conducting film made from conducting ink or paste, or the substrate itself, for example heavily doped silicon. Examples of gate electrode materials include but are not restricted to aluminum, gold, silver, chromium, indium tin oxide, conductive polymers such as polystyrene sulfonate-doped poly(3,4-ethylenedioxythiophene) (PSS-PEDOT), and conducting ink/paste comprised of carbon black/graphite. The gate electrode can be prepared by vacuum evaporation, sputtering of metals or conductive metal oxides, conventional lithography and etching, chemical vapor deposition, spin coating, casting or printing, or other deposition processes. The thickness of the gate electrode ranges for example from about 10 to about 200 nanometers for metal films and from about 1 to about 10 micrometers for conductive polymers. Typical materials suitable for use as source and drain electrodes include those of the gate electrode materials such as aluminum, gold, silver, chromium, zinc, indium, conductive metal oxides such as zinc-gallium oxide, indium tin oxide, indium-antimony oxide, conducting polymers and conducting inks. Typical thicknesses of source and drain electrodes are, for example, from about 40 nanometers to about 1 micrometer, including more specific thicknesses of from about 100 to about 400 nanometers.

Typical materials suitable for use as source and drain electrodes include those of the gate electrode materials such as gold, silver, nickel, aluminum, platinum, conducting polymers, and conducting inks. In specific embodiments, the electrode materials provide low contact resistance to the semiconductor. Typical thicknesses are about, for example, from about 40 nanometers to about 1 micrometer with a more specific thickness being about 100 to about 400 nanometers. The OTFT devices of the present disclosure contain a semiconductor channel. The semiconductor channel width may be, for example, from about 5 micrometers to about 5 millimeters with a specific channel width being about 100 micrometers to about 1 millimeter. The semiconductor channel length may be, for example, from about 1 micrometer to about 1 millimeter with a more specific channel length being from about 5 micrometers to about 100 micrometers.

The source electrode is grounded and a bias voltage of, for example, about 0 volt to about 80 volts is applied to the drain electrode to collect the charge carriers transported across the semiconductor channel when a voltage of, for example, about +10 volts to about −80 volts is applied to the gate electrode. The electrodes may be formed or deposited using conventional processes known in the art.

If desired, a barrier layer may also be deposited on top of the TFT to protect it from environmental conditions, such as light, oxygen and moisture, etc. which can degrade its electrical properties. Such barrier layers are known in the art and may simply consist of polymers.

The various components of the OTFT may be deposited upon the substrate in any order. Generally, however, the gate electrode and the semiconducting layer should both be in contact with the gate dielectric layer. In addition, the source and drain electrodes should both be in contact with the semiconducting layer. The phrase "in any order" includes sequential and simultaneous formation. For example, the source electrode and the drain electrode can be formed simultaneously or sequentially. The term "on" or "upon" the substrate refers to the various layers and components with reference to the substrate as being the bottom or support for the layers and components which are on top of it. In other words, all of the components are on the substrate, even though they do not all directly contact the substrate. For example, both the dielectric layer and the semiconducting layer are on the substrate, even though one layer is closer to the substrate than the other layer. The resulting TFT has good mobility and good current on/off ratio.

The following examples are for purposes of further illustrating the present disclosure. The examples are merely illustrative and are not intended to limit devices made in accordance with the disclosure to the materials, conditions, or process parameters set forth therein.

EXAMPLES

Thioxantheno[2,1,9,8-klmna]thioxanthene was prepared by a series of chemical reactions.

First, [1,1'-binaphthalene]-2,2'-dithiol was synthesized as shown below:

[1,1'-binaphthalene]-2,2'-diyl bis(dimethylcarbamothioate) was prepared in two steps according to the procedure described in "Preparation of Enantiomerically Pure 1,1'-Binaphthalene-2,2'diol and 1,1'-Binaphthalene-2,2'dithiol", *J. Org. Chem.* 1993, 58, 1748-1750.

Next, a solution of [1,1'-binaphthalene]-2,2'-diyl bis(dimethylcarbamothioate) (2.00 grams, 4.3 mmol) in a 1:1 mixture of THF (20 mL), MeOH (20 mL) was treated with a solution of KOH (2.42 grams, 43 mmol) in deionized water (20 mL). The reaction was heated at 60° C. under an inert Argon atmosphere. After 24 hours, the heating source was removed and the reaction was cooled to room temperature. The reaction was treated dropwise with glacial acetic acid (3.0 mL) was to acidify the reaction. The crude reaction mixture was then extracted with $CH_2Cl_2$ (3×75 mL). The combined $CH_2Cl_2$ layers were washed with brine (50 mL), dried ($MgSO_4$), filtered and concentrated to dryness using a rotary evaporator. The product was obtained as a foamy solid and was used without further purification. The structure was confirmed using $^1$H NMR spectroscopy.

Next, 2,2'-bis(methylthio)-1,1-binaphthalene was synthesized, as shown below:

A solution of crude [1,1'-binaphthalene]-2,2'-dithiol (1.4 grams, 4.3 mmol) in a 1:1 mixture of $CH_2Cl_2$ (20 mL) and $Et_3N$ (20 mL) was cooled to 0° C under an inert Argon atmosphere. The reaction was treated dropwise with iodomethane (1.4 mL, 22 mmol). After 5 minutes, the cooling bath was removed and the reaction was stirred at room temperature. After 18 hours, the crude reaction mixture was filtered to remove any salts that formed during the reaction and then concentrated using a rotary evaporator. The crude product was purified by column chromatography on silica gel eluting with a 9:1 mixture of ethyl acetate in hexane. The product was isolated an off-white solid and the structure was confirmed by $^1$H NMR spectroscopy.

Next, 2,2'-bis(methylsulfinyl)-1,1'-binaphthalene was synthesized, as shown below:

A solution of 2,2'-bis(methylthio)-1,1'-binaphthalene (0.59 grams, 1.7 mmol) in glacial acetic acid (20 mL) was treated with a 35% hydrogen peroxide solution (0.41 grams, 4.3 mmol) and stirred at room temperature. After 5 hours, the reaction was quenched with water (25 mL). The crude reaction mixture was extracted with ethylacetate (3×50 mL). The combined ethylacetate layers were washed with brine (50 mL), dried (MgSO$_4$), filtered and concentrated to dryness using a rotary evaporator. The product was obtained as a foamy solid and used without further purification. The structure was confirmed using $^1$H NMR spectroscopy.

Finally, thioxantheno[2,1,9,8-klmna]thioxanthene was obtained as shown below:

Trifluoromethanesulfonic acid (2.9 ml, 1.4 mmol) and 2,2'-bis(methylsulfinyl)-1,1'-binaphthalene (0.53 grams, 1.4 mmol) were combined and stirred for 24 hours under an Argon atmosphere. The reaction solution was then carefully added drop-wise to a mixture of water (80 mL) and pyridine (10 mL). The reaction was heated at 100° C. After 1 hour, the red precipitate was filtered off and washed with water and ethanol. The structure of thioxantheno[2,1,9,8-klmna]thioxanthene was confirmed by $^1$H NMR spectroscopy.

It will be appreciated that variants of the above-disclosed and other features and functions, or alternatives thereof, may be combined into many other different systems or applications. Various presently unforeseen or unanticipated alternatives, modifications, variations or improvements therein may be subsequently made by those skilled in the art which are also intended to be encompassed by the following claims.

The invention claimed is:

1. An electronic device comprising:
   a dielectric layer; and
   a semiconducting layer in direct contact with a surface of the dielectric layer,
   wherein the semiconducting layer includes a polymer binder and molecules of a thiaxanthenothiaxanthene compound of Formula (I):

Formula (I)

wherein $R_1$ to $R_{10}$ are independently selected from the group consisting of hydrogen, an alkyl group, a substituted alkyl group, an alkoxy group, an alkylthio group, an alkenyl group, a substituted alkenyl group, an ethynyl group, a substituted ethynyl group, an aryl group, a substituted aryl group, a heteroaryl group, a substituted heteroaryl group, a trialkylsilyl group, a fluorohydrocarbon group, a cyano group and a halogen; and
wherein the molecules of the compound of Formula (I) are predominantly crystalline or liquid crystalline in the semiconducting layer.

2. The electronic device of claim 1, wherein at least one of $R_1$ to $R_{10}$ is not hydrogen.

3. The electronic device of claim 1, wherein $R_2$ and $R_7$ are selected from the group consisting of an alkyl group, a substituted alkyl group, an alkenyl group, a substituted alkenyl group, an ethynyl group, a substituted ethynyl group, an aryl group, a substituted aryl group, a heteroaryl group, a substituted heteroaryl group, and a halogen.

4. The electronic device of claim 3, wherein $R_1$, $R_3$, $R_4$, $R_5$, $R_6$, $R_8$, $R_9$, and $R_{10}$ are hydrogen.

5. The electronic device of claim 3, wherein $R_2$ and $R_7$ are the same.

6. The electronic device of claim 1, wherein the polymer binder is selected from the group consisting of polymethylmethacrylate, polystyrene, poly(a-methyl styrene), poly(4-methyl styrene), poly(a-methyl styrene-co-vinyl toluene), poly(styrene-block-butadiene-block-styrene), polystyrene-block-isoprene-block-styrene ), poly (vinyl toluene), poly (vinyl naphthalene), poly (vinyl pyridine), terpene resin, poly(styrene-co-2,4-dimethylstyrene), poly(chlorostyrene), poly(styrene-co-a-methyl styrene), poly(styrene-co-butadiene) , polycarbazole, polytriarylamine, poly(N-vinylcarbazole), polythiophene, and a mixture thereof.

7. The electronic device of claim 1, wherein the surface of the dielectric layer is modified by an organosilane.

* * * * *